US005767364A

United States Patent [19]
de Silva et al.

[11] Patent Number: 5,767,364
[45] Date of Patent: Jun. 16, 1998

[54] ENDO-1,4-BETA-D-GLUCANASE

[75] Inventors: Jacqueline de Silva; Carl D. Jarman, both of Bedford; David A. Arrowsmith, Northampton; John S. G. Reid; Mary E. Edwards, both of Stirling, all of United Kingdom

[73] Assignee: Unilever Patent Holdings B.V., Netherlands

[21] Appl. No.: 295,657

[22] PCT Filed: Mar. 1, 1993

[86] PCT No.: PCT/GB93/00424

§ 371 Date: Nov. 4, 1994

§ 102(e) Date: Nov. 4, 1994

[87] PCT Pub. No.: WO93/17101

PCT Pub. Date: Sep. 2, 1993

[30] Foreign Application Priority Data

Feb. 28, 1992 [EP] European Pat. Off. ............ 92301707

[51] Int. Cl.$^6$ ................. A01H 1/04; C12N 5/14; C12N 15/00; C07H 17/00
[52] U.S. Cl. ................. 800/205; 435/172.3; 435/240.4; 435/320.1; 435/69.1; 47/58; 47/DIG. 1; 536/24.5; 536/23.2; 536/23.6; 536/24.1; 424/93.2; 424/93.21
[58] Field of Search ................. 536/24.5, 23.2, 536/23.6, 24.1; 435/172.3, 240.4, 320.1, 69.1; 800/205; 47/58, DIG. 1

[56] References Cited

U.S. PATENT DOCUMENTS

| 5,328,999 | 7/1994 | Bennett et al. ............ 536/24.5 |
| 5,516,694 | 5/1996 | Nishitani et al. ............ 435/320.1 |
| 5,569,830 | 10/1996 | Bennett et al. ............ 800/205 |

FOREIGN PATENT DOCUMENTS

| 353191 | 1/1990 | European Pat. Off. |
| 90 09436 | 8/1990 | WIPO |

OTHER PUBLICATIONS

Tezuka, et al: "Construction of a beta-glucanase hyperproducing Bacillus subtilis using the cloned beta-glucanase gene and a multi-copy plasmid". Agricultural and Biological Chemistry, vol. 53, No. 9, 1989, pp. 2335-2339.

Edwards et al: Purification and properties of a novel xyloglucan-specific endo-(1.4)-beta-D-glucanase from germinated naturtium seeds(*Tropaeolum majus* L.).The Journal of Biological Chemistry, vol. 261, No. 20, Jul. 1986, pp. 9489-9494.

Database WPIL, week 9137, Derwent Publications AN 91-271574 [37] & JP-A-3180180, Jun. 8, 1991.

Fanutti et al: A xyloglucan-oligosaccharide-specific.alpha.-D-xylosidase or exo-oligoxyloglucan-.alpha.-xylohydrolase from germinated nasturtium (*Tropaeolum majus* L.) seeds. Purification, propeties and its interaction with a xyloglucan-specific endo-(1, fwdarw.4)-.beta.-D-glucanase and other hydrolases during storage-xyloglucan mobilization, & plants 1991, Chemical Abstracts Database, abstract No. 115(7)67183y, vol. 184, No. 1, pp. 137-147.

*Primary Examiner*—Gary Benzion
*Attorney, Agent, or Firm*—Cushman Darby & Cushman IP Group of Pillsbury Madison & Sutro, LLP

[57] ABSTRACT

A sequence encoding an enzyme having a xyloglucan-specific endo-(1–4)-beta-D-glucanase activity, and functional equivalents thereof, is disclosed. Also disclosed are vectors comprising such sequences, and transgenic plants into which such sequences have been introduced, a method of altering the characteristics of a plant, and a method of producing an enzyme having the activity defined above by means of recombinant DNA technology.

14 Claims, 14 Drawing Sheets

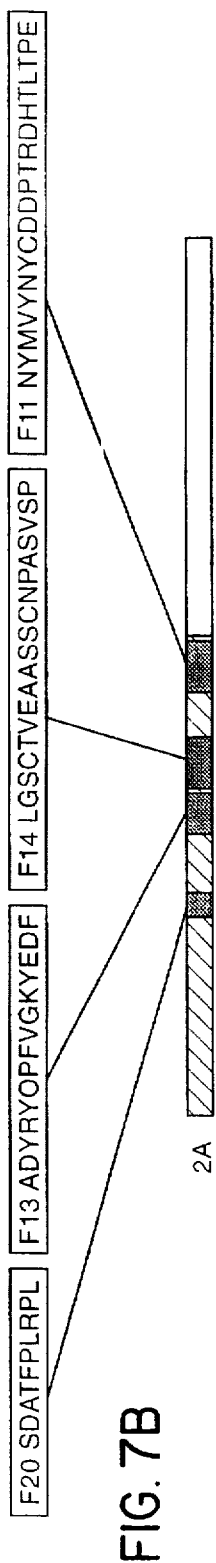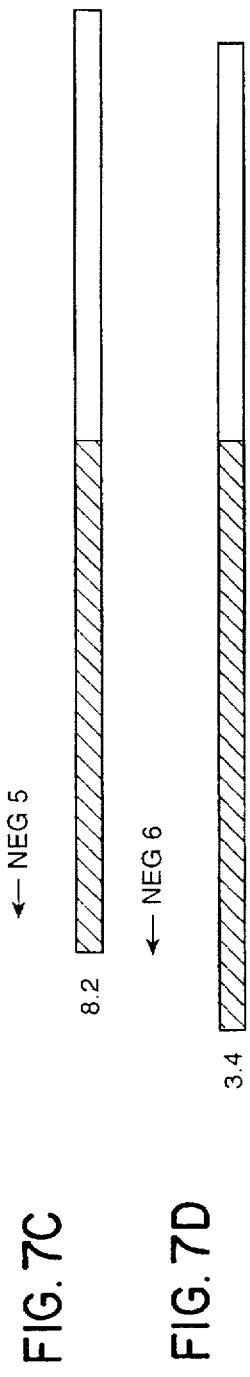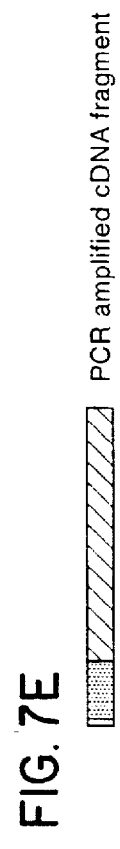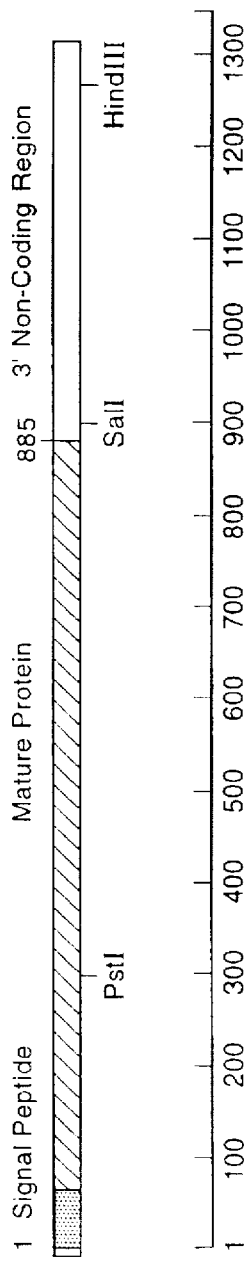

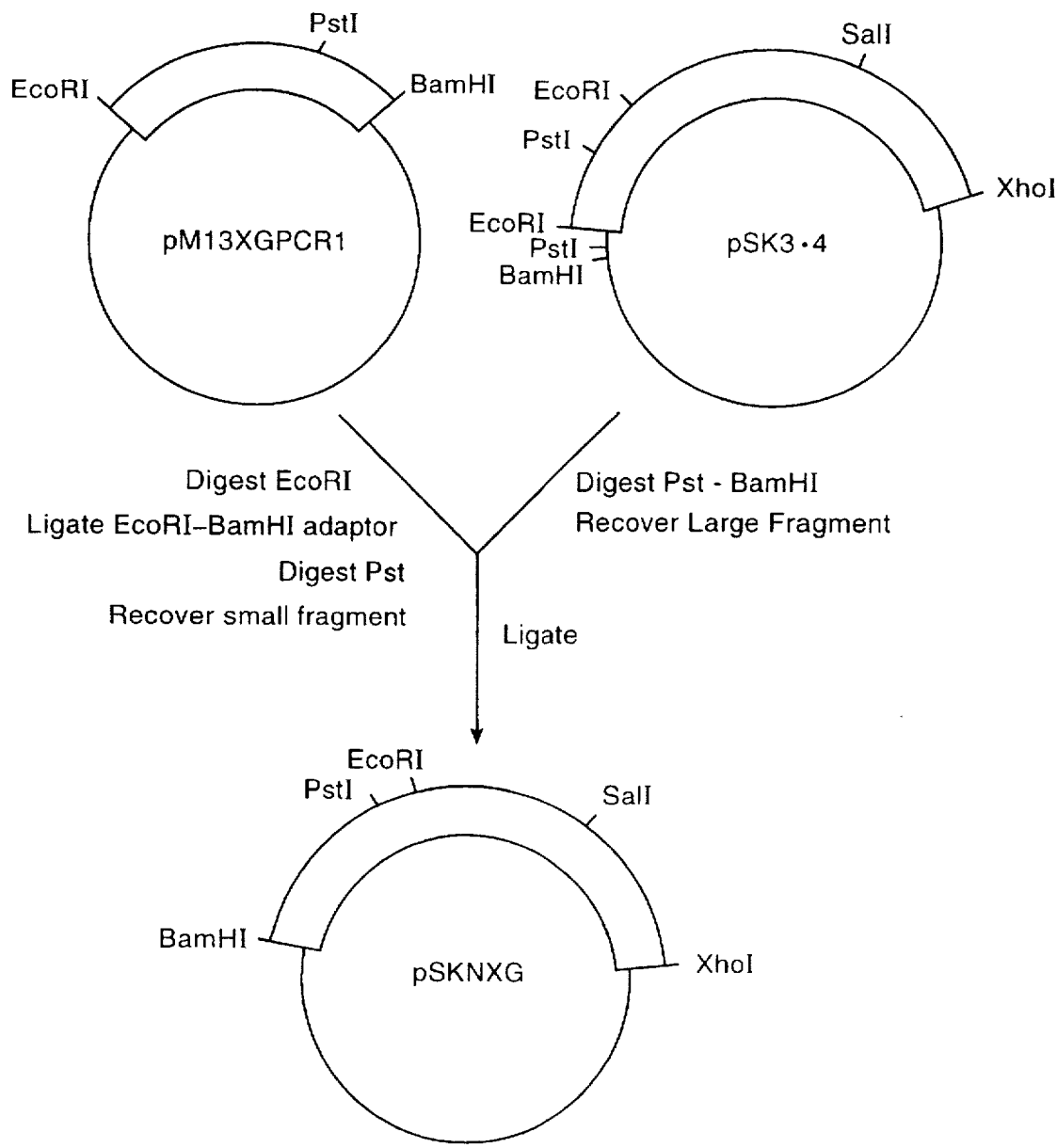

FIG. 9A

```
NXG1        CCTTATTCACTTCACACAAATGCCTTCTCCCTCCATAATGCCTTCCTAACATTCTATCCATTTTTCTT    65
NXG1                                       M  P  P  N  I  L  S  I  F  L        10

NXG1        CATCTTCTTCCTATTCACTAATGTTTTCTTCAAGCTGTTGGGTCAGGCCCACCTTCACCAGGATAT   131
NXG1         H  L  L  P  I  L  M  F  S  S  S  C  L  G  Q  G  P  P  S  P  G  Y    32

NXG1        TACCCTAGTAGCCAAATCACTCCCTAGGCTTGATCAAGGCTATACAAATTTATGGGTCCCTCAA    197
NXG1         Y  P  S  S  Q  I  T  S  L  G  F  D  Q  G  Y  T  N  L  W  G  P  Q    54

NXG1        CATCAAAGGGTAGACCAAGGCTCATTAACAATATGGCTTGATTCTACCTCAGGAAGTGGATTCAAA   263
NXG1         H  Q  R  V  D  Q  G  S  L  T  I  W  L  D  S  T  S  G  S  G  F  K    76

NXG1        TCGATTAACCGATATCGCTCTGGTTACTTCGGTGCTAATATTAAGTTACAATCTGGATACACTGCA   329
NXG1         S  I  N  R  Y  R  S  G  Y  F  G  A  N  I  K  L  Q  S  G  Y  T  A    98

NXG1        GGAGTCATTACAATCTTTCTATCTTTCGAATAACCAAGACTATCCAGGAAAACATGATGAGATCGAT   395
NXG2                                          ..........A........                  45
NXG1         G  V  I  T  S  F  Y  L  S  N  N  Q  D  Y  P  G  K  H  D  E  I  D    120

NXG1        ATTGAATTCCTCGGAACAATACCCGGAAAGCCGTATACATTGCAGACGAATGTTTTTATAGAAGGA   461
NXG2         .........T.............T........C..........                             111
NXG1         I  E  F  L  G  T  I  P  G  K  P  Y  T  L  Q  T  N  V  F  I  E  G    142

NXG1        AGTGGAGATTACAATATAATCGGAAGGGAAATGAGAATTCATTTATGGTTTGATCCAACACAAGAT   527
NXG2         .........................A..T...........                              177
NXG1         S  G  D  Y  N  I  I  G  R  E  M  R  I  H  L  W  F  D  P  T  Q  D    164

NXG1        TATCATAACTATGCTATTTATTGGACACCAAGTGAGATCATATTTTTTGTCGATGATGTACCGATA   593
NXG2         ...........................                                            243
NXG1         Y  H  N  Y  A  I  Y  W  T  P  S  E  I  I  F  F  V  D  D  V  P  I    186

NXG1        AGGAGGTACCCCTAGAAAGAGCGATGCTACATTTCCTTTGAGACCGTTATGGGTGTACGGGTCGGTG   659
NXG2         .....                                                                   309
NXG1         R  R  Y  P  R  K  | S  D  A  T  F  F  P  L  R  P  L |  W  V  Y  G  S  V    208

FROM FIG. 9A

```
NXG1  TGGGACGCGTCTTCTTGGGCTACTGAAAACGGTAAATACAAAGCCGATTATCGATACCAACCTTTT    725
NXG2  ............................................................       375
NXG1   W  D  A  S  S  W  A  T  E  N  G  K  Y  K  A  D  Y  R  Y  Q  P  F    230

NXG1  GTTGGAAAGTACGAAGATTTCAAGTTAGGTTCGTGCACCGTGGAAGCGGCTTCGTCTTTGCAATCCG   791
NXG2  ..................................C...............................  441
NXG1   V  G  K  Y  E  D  F  K  L  G  S  C  T  V  E  A  A  S  S  C  N  P    252

NXG1  GCTTCCGGTATCACCCTTATGGTGGTTCAGTTGAGCCAACAAGTCGCGGCGATGGAATGGGTTCAGAAA  857
NXG2  .....................................................................  507
NXG1   A  S  V  S  P  Y  G  Q  L  S  Q  Q  Q  V  A  A  M  E  W  V  Q  K     274

NXG1  AATTACATGGTTTATAATTATTGTGATGACCCGACCCGAGACCACACGTTAACACCCGAGTGTTAA    923
NXG2  ..................................................................  573
NXG1   N  Y  M  V  Y  N  Y  C  D  D  P  T  R  D  H  T  L  T  P  E  C  .    295

NXG1  GATTTCATGTCGACTAAAAAACAGCAAAGAACAAAAAGTTTTATGGGTTTCAATAATTTTTC         989
NXG2  .........................T.........................T............    639

NXG1  TGAAAAAAATGATTTTCTATTTGGATTTAATTTGATAAAAAAAAAGGGTTTGTTGTTGT           1055
NXG2  ............................................................         698

NXG1     TAATAATGGATGACTTGAGATGGGTCTACTTGCCAAGAAAAGGTGCAAGAGTTGT            1118
NXG2  TGTTGTT......GTT............................................         764

NXG1  TGGGCG   TCCAAGCATTCAAGAACTTTGAAGGTTATGTTGGGGGCTGTGTTTGTTTTTTTA       1180
NXG2  ......ATCG..............................GC.........................  825

NXG1  ATATATGTATAATTGATCATCTTTTATATTTTAAATGAATTTATTGAAT                     1229
NXG2  .............................T.......T.G.....AATGTCTATATATAATA       891

NXG2  TATATATATATATGTATATATATATATATATATGAATAAAAAGGTATATGTAAGTTATATATAGAAGCTT  954
```

ENDO-1,4-BETA-D-GLUCANASE

FIELD OF THE INVENTION

This invention relates to nucleotide sequences encoding a plant enzyme, vectors containing said nucleotide sequences, transgenic plants containing said nucleotide sequences, recombinant DNA methods of producing the enzyme, and methods of altering the properties of a plant.

BACKGROUND OF THE INVENTION

Fruit and vegetable cell walls are largely polysaccharide, the major components being pectin, cellulose and xyloglucan (reference 1). Numerous cell wall models have been proposed which attempt to incorporate the essential properties of strength and flexibility (references 2,3,4).

Xyloglucans are 1,4-beta-glucans that are extensively substituted with alpha-1,6-xylosyl side chains, some of which are 1,2 beta-galactosylated. They are found in large amounts in the primary cell walls of dicots but also in certain seeds, where they serve different roles.

Primary cell wall xyloglucan is fucosylated. It is tightly hydrogen bonded to cellulose microfibrils and requires concentrated alkali or strong swelling agents to release it. Xyloglucan is thought to form cross-bridges between cellulose microfibrils, the cellulose/xyloglucan network forming the major load-bearing/elastic network of the wall. DCB mutated suspension culture cells (cell walls lacking cellulose) release xyloglucan into their media, suggesting that xyloglucan is normally tightly bound to cellulose.

Hydrolysis of primary cell wall xyloglucan has been demonstrated in segments of dark grown squash hypocotyls, during IAA induced growth (reference 15). Endohydrolysis of wall xyloglucan is thought to contribute to wall loosening which accompanies cell expansion (reference 16). The average molecular weight of xyloglucan has also been shown to decrease during tomato fruit ripening and this may contribute to the tissue softening which accompanies the ripening process (reference 17).

Certain seeds, e.g. nasturtium, contain up to 30% by weight of xyloglucan, stored in thickened cotyledonary cell walls, which serves as a reserve polysaccharide and is rapidly depolymerised during germination.

An endo 1,4 beta-D glucanase which specifically acts on xyloglucan (i.e. a xyloglucanase) has been isolated and purified to apparent homogeneity from germinating nasturtium (*Tropaeolum majus L.*) seeds (reference 11).

The purified xyloglucanase gives a single polypeptide band on SDS polyacrylamide gel electrophoresis, (apparent molecular weight, 29–31 kDa) and isoelectric focusing (isoelectric point, 5.0). The enzyme displays an absolute specificity for xyloglucan and an endo mode of action, as determined by end product analysis following hydrolysis of tamarind seed xyloglucan (reference 15). Although the natural substrate of the enzyme is nasturtium cotyledonary reserve xyloglucan, it has also been shown to hydrolyse fucose containing primary cell wall xyloglucans in vitro (reference 11). At high substrate concentrations, xyloglucan endo-transglycosylase (XET) activity has been demonstrated (reference 18).

Similar enzyme activity has been detected in other plant tissue and shown to be positively correlated with growth rate in different zones of the pea stem (reference 19). It has been proposed that XET is responsible for cutting and rejoining intermicrofibrillar xyloglucan chains and that this causes the wall-loosening required for plant cell expansion. XET activity has also been demonstrated in tomato fruit (xyloglucanase activatable by xyloglucan oligosaccharides) where it is reportedly highest at the "breaker" stage of ripening (reference 20) and may be involved in the softening process.

This Application describes the isolation of a xyloglucan specific endo- (1–4)-Beta-D-glucanase (xyloglucanase/XET) gene from nasturtium. The enzyme encoded by this novel nucleotide sequence is highly specific for xyloglucan (reference 11).

SUMMARY OF THE INVENTION

In one aspect the invention provides a nucleotide sequence, encoding an enzyme having a xyloglucan-specific endo-(1–4)-Beta-D-glucanase activity, comprising nucleotides 35-919 of the sequence NXG1 shown in FIGS. 9A and 9B (Seq. ID No. 1) or functional equivalents thereof.

As will be apparent to those skilled in the art, functional equivalents of the nucleotide sequence of the invention include, for example: those nucleotide sequences which encode the same polypeptide (but which, but which by virtue of the degeneracy of the genetic code, possess a different nucleotide sequence); sequences which encode substantially the same polypeptide but wherein there may be one or more conserved amino acid substitutions (i.e. the substitution of an amino acid for one with similar properties); sequences which encode substantially the same polypeptide (which preferably share at least 50% amino acid homology and more preferably at least 60% homology) but wherein there may be one or more minor deletions or truncations; and sequences which hybridize under standard conditions to the complement of nucleotides 35-919. Typically such functional equivalents will have at least 75% nucleotide sequence homology and preferably at least 85% homology. An example of a functional equivalent is the sequence NXG2 (Seq. ID No. 2) shown in FIGS. 9A and 9B.

A particular example of a functional equivalent is the sequence comprising the antisense equivalent to the sequence of the invention. Whilst antisense sequences are not generally understood to be functional equivalents, use of the term functional equivalent is intended for the purposes of the present application to encompass such sequences.

Preferably the sequence also comprises a suitable 5' untranslated region, including a promoter, to enable expression in appropriate host cells.

Preferably the sequence also comprises a suitable 3' untranslated region, comprising a "stop" codon substantially immediately adjacent to the 3' end of the sequence of the invention. As well as a stop codon the 3' untranslated region can comprise other signals, such as a polyadenylation signal. Conveniently the 3' untranslated region comprises nucleotides 920–1055 of the sequence NXG1 shown in FIGS. 9A and 9B (Seq. ID No. 1).

Conveniently the sequence comprises part of a gene.

An example of such a gene is that from Nasturtium (*Tropaeolum majus L.*), the cDNA of which has been cloned and sequenced by the inventors.

In another aspect the invention provides a vector comprising the sequence shown in FIGS. 9A and 9B or functional equivalents thereof. It might be desirable to produce large quantities of the enzyme by operably linking the sequence defined above to a suitable promoter in such a vector. For instance, xyloglucanases are known to be useful in modifying xyloglucans from tamarind seeds.

Thus, in a further aspect, the invention provides a method of producing the enzyme comprising the steps of: inserting a sequence encoding the enzyme or functional equivalents thereof into a suitable vector, transforming a host cell with said vector, growing the host cell in suitable culture conditions so that the enzyme is expressed, followed by obtaining the enzyme from either the culture medium and/or the host cells.

Preferably the host cell is a micro-organism. It is also preferable, but by no means essential, that the host cell is eukaryotic, as a eukaryotic host is more likely to express the enzyme in a fully functional conformation.

Suitable vectors are known which can be used to introduce and express the sequence of the invention in plants.

The plant could be, for example, a plant which does not normally possess a nucleotide sequence in accordance with the invention. Alternatively, a sequence in accordance with the invention could be introduced into a plant which already possesses one or more such sequences. The introduction of one or further such sequences could be used to modify the expression of the xyloglucanase.

Thus in another aspect the invention provides a plant, into which has been introduced the sequence of the invention or a functional equivalent thereof.

It will be readily apparent to those skilled in the art that expression of the sequence of the invention or functional equivalents thereof in a plant in which such expression does not naturally occur, or in which such expression occurs at different levels, may alter the characteristics of the plant, due to the activity of the enzyme encoded by the sequence. Equally, transcription into mRNA of the complement of the sequence of the invention (a particular example of a functional equivalent), to make antisense RNA, could interfere with the expression of the endogenous xyloglucanase gene in a transgenic plant and thereby reduce levels of xyloglucanase activity.

Thus in a further aspect the invention provides a method of altering the characteristics of a plant or part thereof, comprising introducing into the plant the sequence of the invention or a functional equivalent thereof, so as to alter the level of xyloglucanase activity.

The altered plant is preferably any commercially important plant (including fruit or vegetable plants) where there is sufficient knowledge to perform the method of the invention and in which xyloglucan has a structural function (i.e. dicots and non-Graminaceous monocots).

Such plants include:

alfalfa, apple, brocolli, cabbage, carrot, cauliflower, celery, cotton, cranberry, cucumber, eggplant, flax, grape, horseradish, kiwi, lettuce, mangoes, melon, oilseed rape, papaya, pea, peaches, pears, peppers, plum, poplar, potato, raspberry, soybean, spruce, strawberry, sugarbeet, sweet potato, tobacco, tomato, walnut.

It will be appreciated that the characteristics of the whole plant need not be altered. It may be desirable to alter the properties of parts of the plant (e.g. seeds, fruit). This could be achieved, for example, by the use of tissue-specific promoters to regulate transcription of the introduced sequence.

The method of the invention would be expected to alter levels of xyloglucanase activity and the average molecular weight of xyloglucans in the relevant part of the plant. Moreover, in view of the important structural role of xyloglucan, one might expect the characteristics which might be altered to include: size, rate of growth, texture, or speed of ripening.

BRIEF DESCRIPTION OF THE DRAWINGS

The invention is further described by reference to the following illustrative Examples and drawings, in which.

FIGS. 7A to 7F show the relationship of the various Nasturtium xyloglucanase cDNA clones.

FIG. 8 shows the method used to construct a plasmid comprising a full-length xyloglucanase coding sequence.

FIGS. 9A and 9B show the nucleotide sequence of the complete xyloglucanase cDNA sequence (NXG1)(Seq. ID No. 1), a functional equivalent (NXG2)(Seq. ID No. 2) and the amino acid sequence (NXG1, Seq. ID No. 3) encoded by the nucleotide sequences.

DETAILED DESCRIPTION OF THE FIGURES

Figures 1A, 1B:
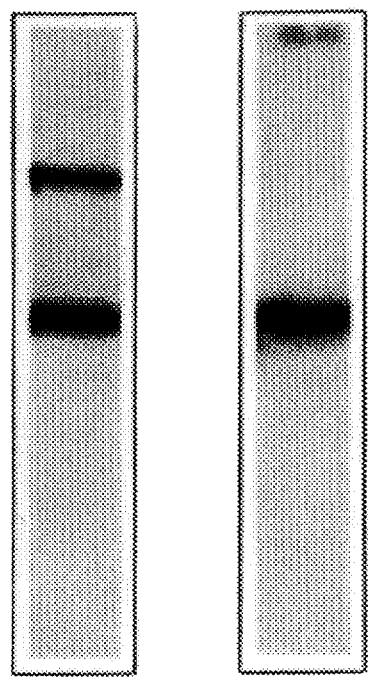
FIGS. 1A, 1B and 2 are photographs of an immunoblot probed with crude (1A) or affinity purified (1B and 2) anti-xyloglucanase antibody.

FIGS. 1A and 1B

Xyloglucanase activity has been shown to peak at 12-14 days after germination, coincident with the rapid degradation of stored reserves of xyloglucan. In order to establish whether this represents de novo synthesis of xyloglucanase, protein levels were quantified throughout germination using Western blotting.

Crude extracts of 12 day germinating seeds were blotted (along with known quantities of antigen) against a crude polyclonal antibody raised at the University of Stirling. A strongly cross-reacting polypeptide was identified at 31 kDa, which represented approximately 0.5% of the total seed protein. A second polypeptide at 45-46 kDa also cross-reacted with the crude serum (FIG. 1A).

The crude antibody was affinity purified using gel fractionated xyloglucanase (31 kDa). Protein (25 ug) was concentrated by vacuum drying, fractionated by PAGE and blotted onto nitrocellulose filters as described above. Filters were stained using 0.1% Ponseau S (in 1% acetic acid) and destained in 1% acetic acid. Antigen bound strips of nitrocellulose were washed (5×5 minutes) in Tris buffered Saline (TBS), incubated for 20 hours at 4° C. in TBS, 15% haemoglobin, 2.5% crude antibody, then rinsed in TBS. Antibody was released in 0.2M glycine pH 2.8 which was then neutralised with either 1M NaOH or 1M Tris-HCl pH 8. The affinity purified antibody no longer recognised the larger polypeptide on blots of seed extract (FIG. 1B) suggesting that it may have been a minor contaminant of the original antigen preparation, which was immunologically unrelated to xyloglucanase.

FIG. 2

Figure 2:
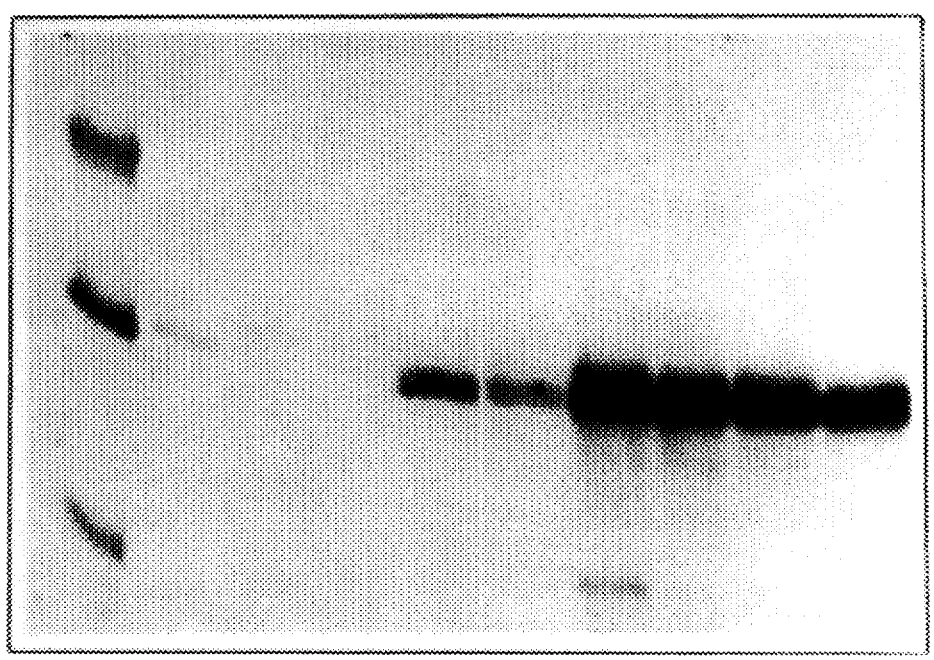

The affinity purified antibody was used to quantify xyloglucanase levels throughout germination. Levels initially rose sharply, peaking at approximately 11 days (FIG. 2) after germination. This coincides with the peak in xyloglucanase activity previously reported in germinating nasturtium suggesting that the enzyme is synthesised de novo during seed germination.

FIG. 3

Nasturtium cotyledons (2 g) were roughly ground in a Moulinex blender in the presence of dry ice, and then ground to a fine powder using a pestle and mortar, in the presence of liquid nitrogen. RNA was isolated largely as described by Hall (reference 12) except that the re-suspended LiCl precipitate was extracted twice with phenol/chloroform (1:1).

Routinely, 500 ug of spectrophotometricaly clean RNA was obtained from 2 g of germinating *nasturtium* cotyledons. RNA was judged to be largely intact by agarose gel electrophoresis.

Figure 3:
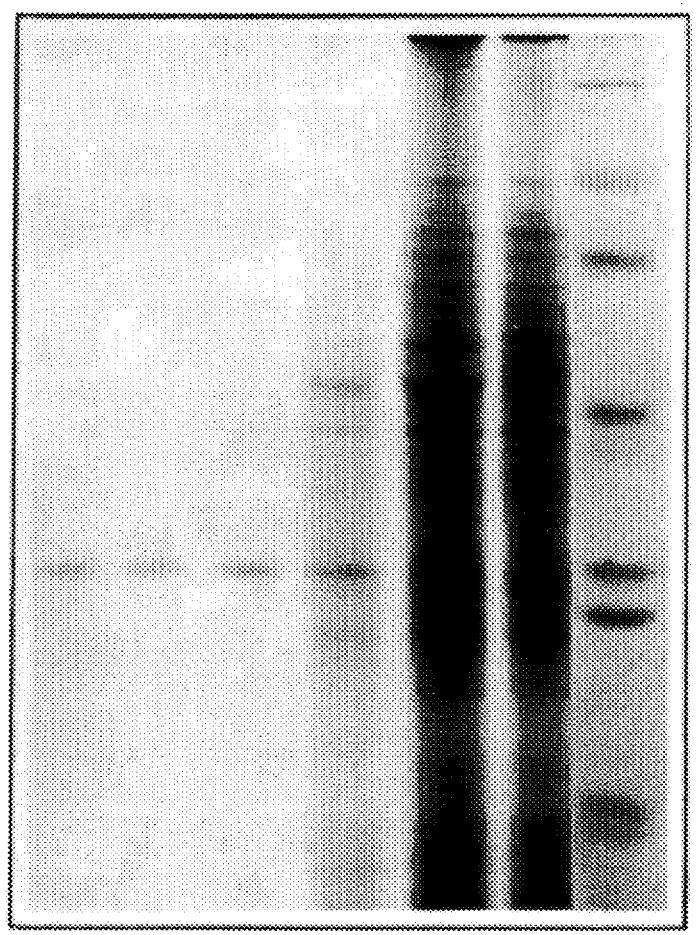
FIG. 3 is a photograph of SDS-PAGE analysis of Nasturtium seed RNA in vitro translation products (lanes 5 and 6) immunoprecipitated using anti-xyloglucanase antibody (lanes 1-3).

Total RNA was translated in vitro using a cell free, nuclease depleted, wheat germ translation system, supplied by Amersham International. Routinely, a mix was prepared containing 12 ul 1M potassium acetate, 8 ul minus methionine amino acid mix, 10 ul $^{35}$S-methionine (Amersham International, 800Ci/mmol), 34 ul $H_2O$ and 60 ul wheat germ extract. 1 ul of total RNA (10 ug) was incubated with 14 ul of the wheat germ mix for 60 minutes at 25° C. Translation mixes (10 ul) were boiled for 1 minute in 100 ul $H_2O$/SDS (0.1%, 0.5%, 1% or 2% SDS) then incubated with 900 ul of immunoprecipitation buffer (1% Triton X-100, 50 mM Tris-HCl pH 8.0, 0.3M NaCl)+/− 1 ul antibody for 3 hours at 20° C. Protein A-Sepharose (1 mg) was added and the incubation continued for a further 1 hour prior to collecting the precipitated antigen-antibody/Protein A-Sepharose complexes by centrifugation in a bench top microcentrifuge. The pellet was washed twice with immunoprecipitation buffer and once with 50 mM Tris-HCl pH 8.0, then boiled in 1×Laemmli sample buffer and analyzed by PAGE. The results are shown in FIG. 3, which shows if translation products were immunoprecipitated in the presence of 2% SDS (lane 1), 1% SDS (lane 2), 0.5% SDS (lane 3), 0.1% SDS (lane 4), in the absence of SDS (lane 5) and in the absence of antibody (lane 6). Lane 7 contains protein molecular weight markers (from Amersham) and immunoprecipitated xyloglucanase. At 0.5% SDS or above, a single polypeptide, with an apparent molecular weight on SDS gels of 33.5 kDa, was immunoprecipitated (tracks 1–3, about half way down the gel) by the affinity-purified anti-xyloglucanase antibody.

Immunoprecipitated xyloglucanase is 2.5 kDa larger than the mature protein detected in seed extracts (31 kDa). This finding is consistent with xyloglucanase being synthesised as a precursor, with an N-terminal signal peptide to target it to the cell wall.

FIG. 4

Figure 4:
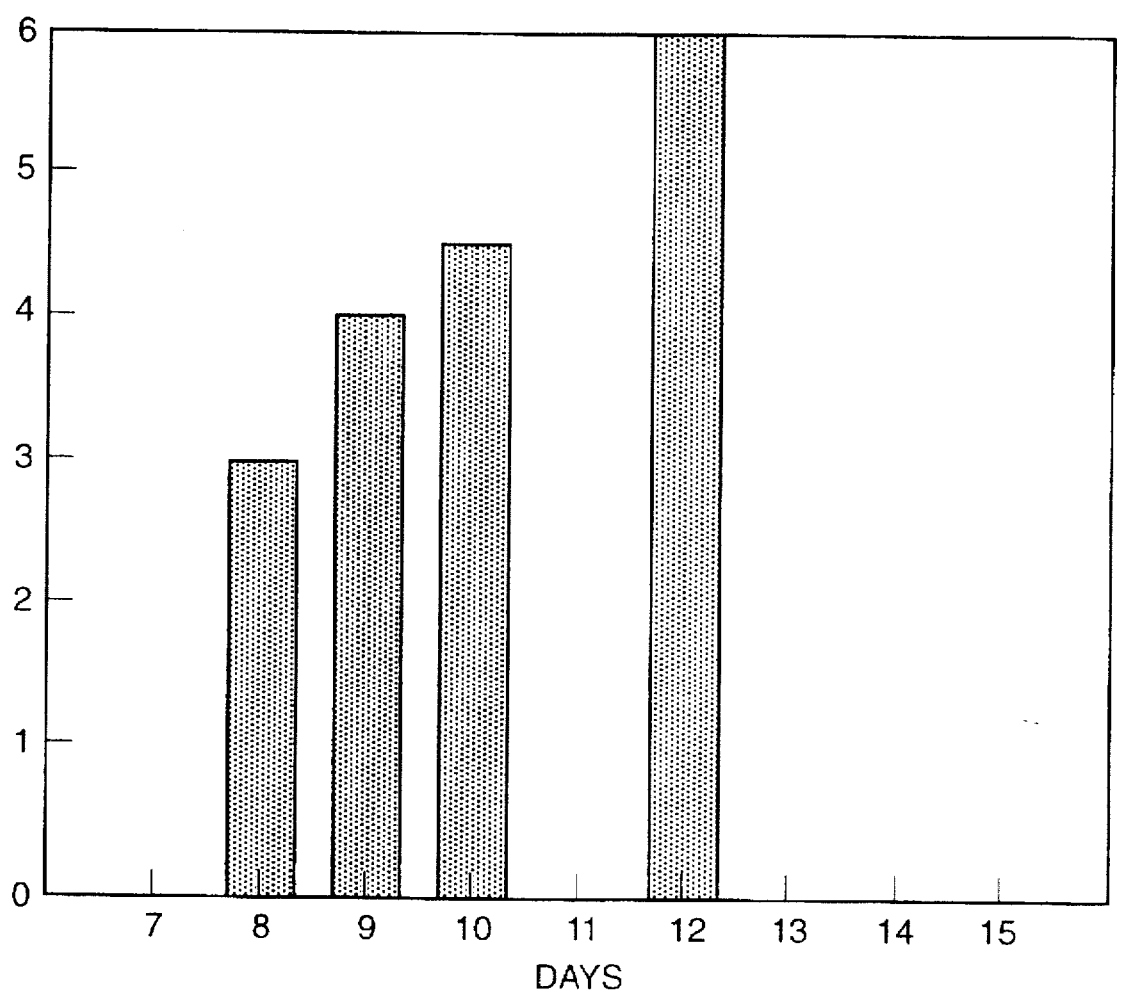
FIG. 4 shows levels of xyloglucanase expression in Nasturtium seeds against time.
Figure 5A:
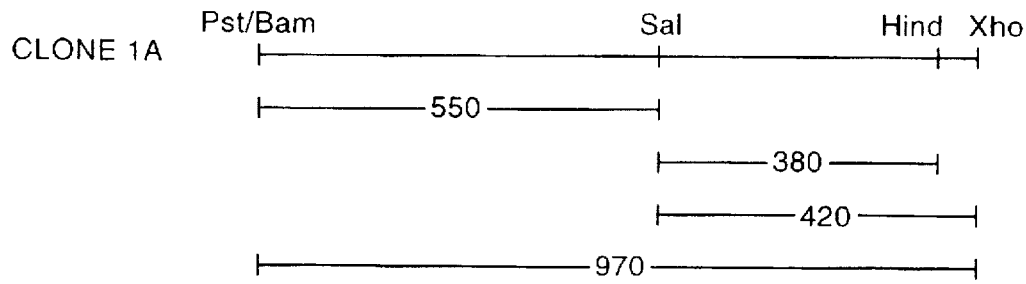
FIGS. 5A to 5D show the results of restriction enzyme analysis of Nasturtium cDNA clones.
Figure 5B:
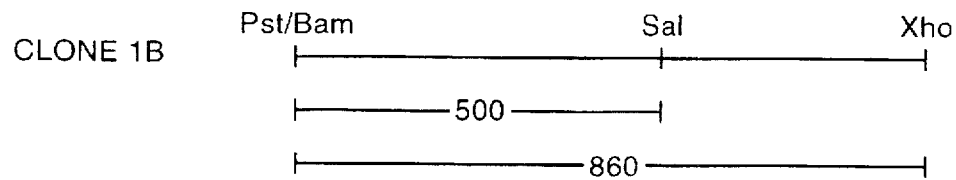
Figure 5C:
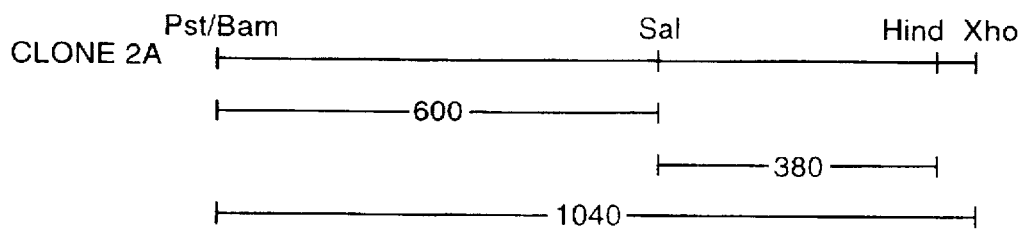
Figure 5D:
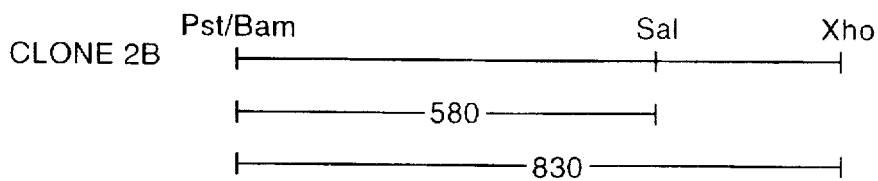

Total RNA was isolated from 8, 9, 10 and 12 day germinating nasturtium seeds. 10 ug of RNA was translated in vitro and radiolabelled xyloglucanase precursor immunoprecipitated using anti-xyloglucanase antibody and protein A-sepharose beads. Xyloglucanase levels were quantified by PAGE followed by fluorography and scanning laser densitometry. The results, presented in histogram form (FIG. 4), show that levels of xyloglucanase mRNA increase during germination, reaching a peak at 12 days, in concert with both xyloglucanase protein levels and enzyme activity.

FIGS. 5A to 5D

Numerous 12 day total RNA preparations were pooled and 20 ug poly $A^+$ RNA isolated by poly U sepharose chromatography. Poly U sepharose was obtained from BRL and columns prepared according to the manufacturers instructions. RNA (up to 4 mg) was loaded onto the column in binding buffer (0.2M NaCl, 10 mM Tris-HCl pH 7.5, 1 mM EDTA, 0.2% SDS) which was then used to wash the column until the $OD_{260}$ of the fractions collected was negligible. Poly A+ RNA was then washed from the column in elution buffer (90% formamide, 10 mM Tris-HCl pH 7.5, 1 mM EDTA, 0.2% SDS) and concentrated by ethanol precipitation.

2.5 ug of poly $A^+$ RNA was used to construct a cDNA library in the cloning vector, lambda ZAPII (purchased from Stratagene and used according to the manufacturer's instructions). The main advantages of this vector are that it provides for directional cDNA cloning and rapid subcloning via in vivo excision. The titre of the resultant library was approximately one million clones, of which an estimated 75% were recombinants.

Part of the library (40,000 clones) was immediately plated and amplified.

20,000 clones were plated using *E. coli* SURE cells and screened with the crude anti-xyloglucanase antibody. Four positively reacting clones were identified. Phage stock corresponding to these positives was recovered and plaque purified by subsequent rounds of plating and screening.

Plasmid DNA was in vivo excised, propagated and subjected to a limited restriction analysis (FIGS. 5A to 5D). All 4 clones were found to contain an internal Sal1 site. The 2 largest clones had a HindIII site close to the 3' end. The cDNA inserts of all 4 clones were excised by digestion with BamH1 and Xho1 and Southern blotted with a xyloglucanase specific oligonucleotide probe.

Xyloglucanase peptide F11: Asn Tyr Met Val Tyr Asn Tyr (part of Seq. ID No. 4)

NEG1 Oligonucleotide mix: TTA ATA TAC CAN ATA TTA AT (Seq. ID. No. 5), plus G G G G variants including G at one or more of the positions shown.

All 4 cDNA inserts hybridised to the xyloglucanase specific probe (result not shown).

Figure 6A:
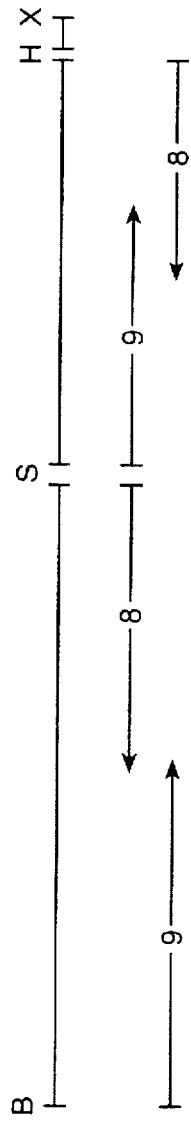
FIGS. 6A to 6C show the subcloning and sequencing strategy for cDNA clone 2A.
Figure 6B:
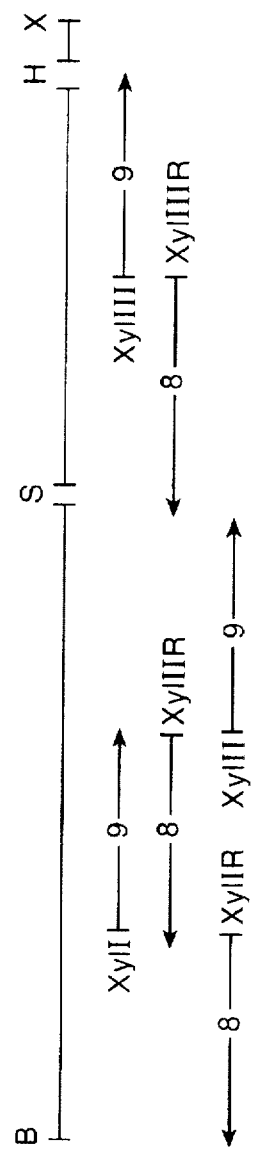
Figure 6C:
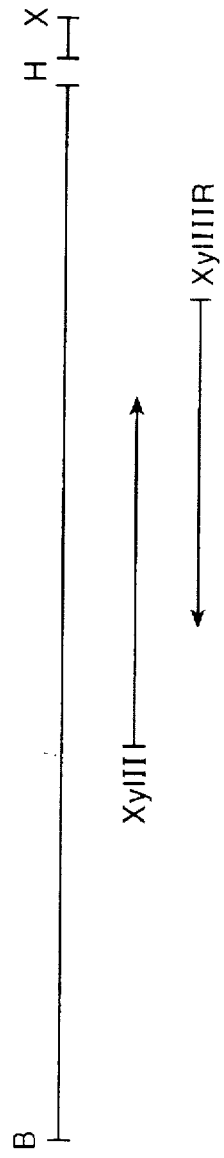

FIGS. 6A to 6C

The largest clone (2A) was subjected to M13 subcloning and DNA sequence analysis (FIGS. 6A to 6C). Using 6 gene specific internal DNA primers, the insert (EcoR1-HindIII) was completely sequenced in both directions. The sequenced fragment is 914 p in length and contains an open reading frame (ORF) of 528 nucleotides (176 amino acids).

FIGS. 7A to 7F

Four xyloglucanase lysC peptides, F11, F13, F14 and F20 (Seq. ID Nos. 4, 6, 7 and 8 respectively) were located within the 2A ORF, confirming its identity as a xyloglucanase cDNA clone (FIG. 7A). Furthermore, all 4 peptides were preceded in the deduced amino acid sequence by a lysine residue.

The size of xyloglucanase transcript was estimated from Northern blots to be approximately 1.5 kb (data not shown), which is large enough to encode the xyloglucanase precursor immunoprecipitated from nasturtium in vitro translations. This 33.5 kDa protein (approximately 290 amino acids) is likely to be encoded by an ORF of some 870bp. These findings, together with the absence of a 5' translation initiation signal, suggest that 2A is a partial xyloglucanase clone with a substantial part of the 5' coding region and the 5' non-coding region missing.

In an attempt to isolate full-length xyloglucanase clones from the nasturtium cDNA library, an oligonucleotide (NEG5) was synthesised which corresponds to the 5' end of, (Seq. ID. No. 9 in the attached sequence listing.)(Seq. ID No. 9)

NEG5: CCAGGTATTGTTCCGAGAAATTCAATATCG (antisense)

This was radiolabelled and used to screen both the primary and the amplified cDNA libraries. A number of "putative" positive clones were identified, however, these were all eliminated on subsequent rounds of NEG5 screening.

100,000 clones of the amplified library (representing approximately 40,000 primary clones) were screened with the anti-xyloglucanase antibody and 78 positive clones were identified. For handling purposes these were divided into 2 groups, A and B, containing 20 and 58 clones respectively.

20 phage stocks, containing putative positive clones from the antibody screen, (group A) were recovered and plaque purified by subsequent rounds of antibody screening. Plaque pure phage stocks were then screened with the 5' specific xyloglucanase oligonucleotide probe, NEG5. 9 out of the 20 clones gave a positive signal with NEG5. Plasmid DNA for these clones was in vivo excised and analyzed by digestion with the restriction enzymes BamH1 and Sal1. This confirmed the presence of internal Sal1 restriction sites in 8 out of the 9 clones, and identified clone 8.2 as having the longest 5' region. The BamH1-Sal1 fragment of 8.2 was cloned into M13 mp9 and sequenced using an M13 universal primer. Clone 8.2 was found to be 40 bp longer (at the 5' end) than 2A (FIG. 7C).

A second 5' specific xyloglucanase oligonucleotide (NEG6) was synthesised, corresponding to nucleotides 4 to 26 of clone 8.2.

NEG6: CCTGGATAGTCTTGATTATTCGA (antisense) (Seq. ID No. 10)

NEG6 contains 9/23 GC nucleotides and corresponds to a region which lies "upstream" of the majority of xyloglucanase clones in the ZAPII library. It was designed to facilitate the isolation of a full-length xyloglucanase cDNA by either:

i) PCR amplification,
ii) mRNA priming, or
iii) oligonucleotide screening.

58 phage stocks containing putative positive clones from the antibody screen (group B) were recovered. The cDNA inserts (5' ends) of the positive clones were amplified using a polymerase chain reaction. This was carried out using 5 ul of 10–50% plaque pure phage stock or 5 ul of amplified cDNA library stock ($10^{-2}$ dilution). Repeat amplification of PCR products was carried out using gel purified DNA re-suspended in 15 ul $H_2O$. Reactions were carried out using 50 pmol sense and antisense primers, 20 mMdNTPs and 2.5 units Taq polymerase (Stratagene) in 100 ul of buffer (10 mM Tris-HCl pH 8.3, 50 mM KCl, 1.5 mM $MgCl_2$, 0.01% [w/v] gelatin).

Partially pure phage stock and gel purified DNA was amplified using 30 cycles of 94° C. for 30 seconds (denaturing), 55° C. for 20 seconds (annealing) and 72° C. for 30 seconds (extension).

cDNA library stock was amplified using the following steps:
95° C. for 2 minutes
1 cycle of 95° C./2 minutes, 55° C./20 seconds, 72° C./2 minutes,
5 cycles of 95° C./30 seconds, 55° C./20 seconds, 72° C./2 minutes,
24 cycles of 95° C./30 seconds, 55° C./20 seconds, 72° C./30 seconds,
72° C. for 5 minutes,
hold at 4° C.

Initially 21 mer primers (approximately 50% GC rich) were used:

1) XPCR1 GACCATGATTACGCCAAGCTC (Bluescript vector)(Seq. ID No. 11)
2) XPCR2 TGTTGTTGGCTCAACTGACCA (antisense xyloglucanase)(Seq. ID No. 12)

The amplified cDNA fragments were analyzed by agarose gel electrophoresis and the 5 longest clones identified.

The cDNA inserts of the 5 longest clones (5' ends) were amplified using a second polymerase chain reaction. XPCR1 and NEG6 primers were used in order to confirm that the clones were longer than 8.2.

The BamH1-Sal1 fragment of clone 3.4 (pSK3.4) was subcloned into M13 mp9 and mp8 and sequenced using an M13 universal primer and NEG6 respectively. Xyloglucanase identity was confirmed by sequence overlap with clones 2A and 8.2. The cDNA insert of clone 3.4 was 74 bp longer than 8.2 (at the 5' end), but not long enough to contain the complete xyloglucanase ORF (FIG. 7D).

The amplified ZAPII library stock was used as a template for PCR amplification of xyloglucanase clones, using XPCR1 and XPCR2.

This confirmed that the majority of xyloglucanase clones in the library were similar in length to 2A, i.e. partial clones, but that the library also contained a small proportion of larger clones.

A second amplification was carried out using XPCR1 and NEG6B (BamH1 site at the 5' end of NEG6, to facilitate cloning of amplified products):

NEG6B: GAGGATCCTGGATAGTCTTGATTATTCGA (Seq. ID No. 13)

The NEG6B primer lies upstream of the 5' end of clone 2A and should therefore be specific for the minority of longer xyloglucanase clones in the library. PCR gave a number of bands which were gel purified and re-amplified to yield pure DNA for subcloning. Fragments of 450 bp (1) and 250 bp (2) were digested with EcoR1 and BamH1 and cloned into M13 mp8 and mp9. The plasmid pM13XGPCR1.was constructed by cloning the larger fragment into M13 mp9. The larger fragment was sequenced and the cDNA portion found to be 346 bp in length and have a 75 bp overlap with cDNA clone 3.4. FIG. 7 illustrates the overlap between cDNA clones 2A, 8.2 and 3.4 and the PCR amplified cDNA fragment.

FIG. 8

Double stranded DNA (RF) of pM13XGPCR1 was prepared and an EcoR1-Pst1 fragment, containing the 5' end of the cDNA, was recovered. This was ligated into EcoR1-BamH1 cut pSK3.4 (this plasmid was formed by in vivo excision of the 3.4 cDNA clone from the lambda ZAP II library), using an EcoR1 - BamHI adaptor, to produce pSKNXG (FIG. 8).

FIG. 9

FIG. 9 shows the nucleotide sequence (NXG1)(Seq. ID No. 1) of the full length nasturtium xyloglucanase cDNA. NXG1 is derived from the PCR amplified cDNA fragment (nucleotides 1–353) and cDNA clone 3.4 (FIG. 7d, nucleotides 279–1229). There is thus a 75 bp (perfectly homologous) overlap between the PCR fragment and clone 3.4. It is approximately 1300 bp long and contains an ORF of 885 bp (295 amino acids). The boxed regions show the location of peptides F20(Seq. ID No. 8), F13(Seq. ID No. 6), F14(Seq. ID No. 7) and F11(Seq. ID No. 4) illustrated in FIG. 7A. Another in-frame ATG triplet occurs 18 bp upstream from the start of the sequence shown. The sequence 5' to this other ATG codon agrees less closely with the consensus sequence for a plant translation start signal but is a possible candidate. It is anticipated that if this alternative ATG codon was the actual translation initiation codon, the resulting gene product would be a functional equivalent of the sequence of the invention.

The polypeptide sequence (NXG1)(Seq. ID No. 3) encoded by NXG1 is also shown in FIGS. 9A and 9B, using the single letter amino acid code. Shown for comparison are those sequence differences between NXG1 and NXG2. NXG2 is a functional equivalent derived from the cDNA clones 2A (FIG. 7B, nucleotides 41–954) and 8.2 (FIG. 7C), which is 40 bp longer than clone 2A at the 5' end.

FIGS. 10–18

Figure 10:
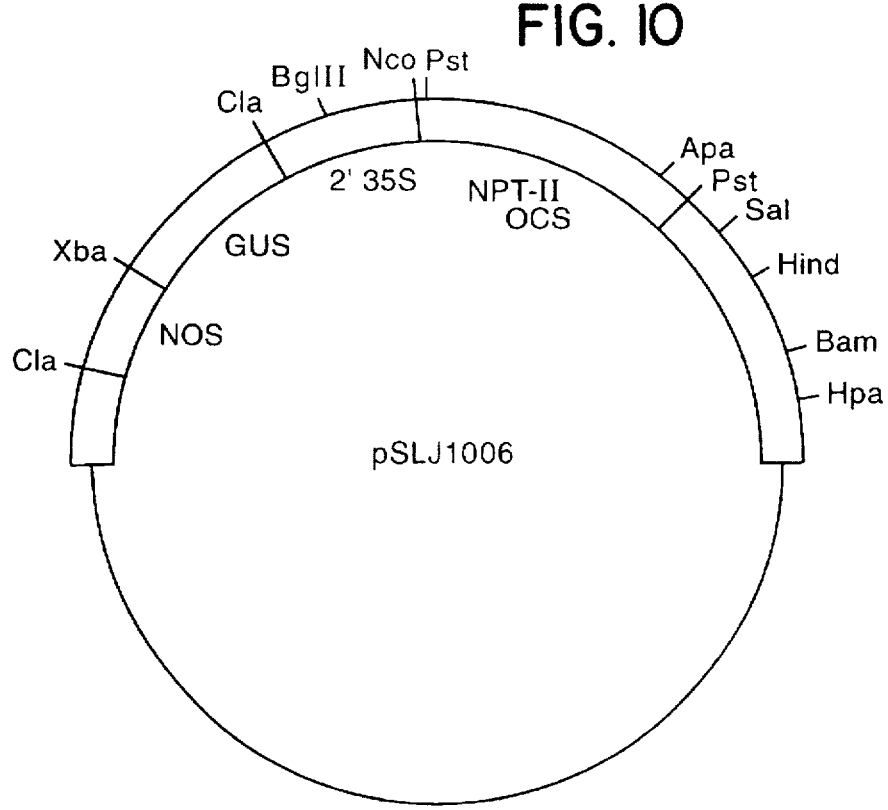
FIGS. 10-18 show various maps of plasmids used in order to construct sense and antisense plant expression vectors.
Figure 11:
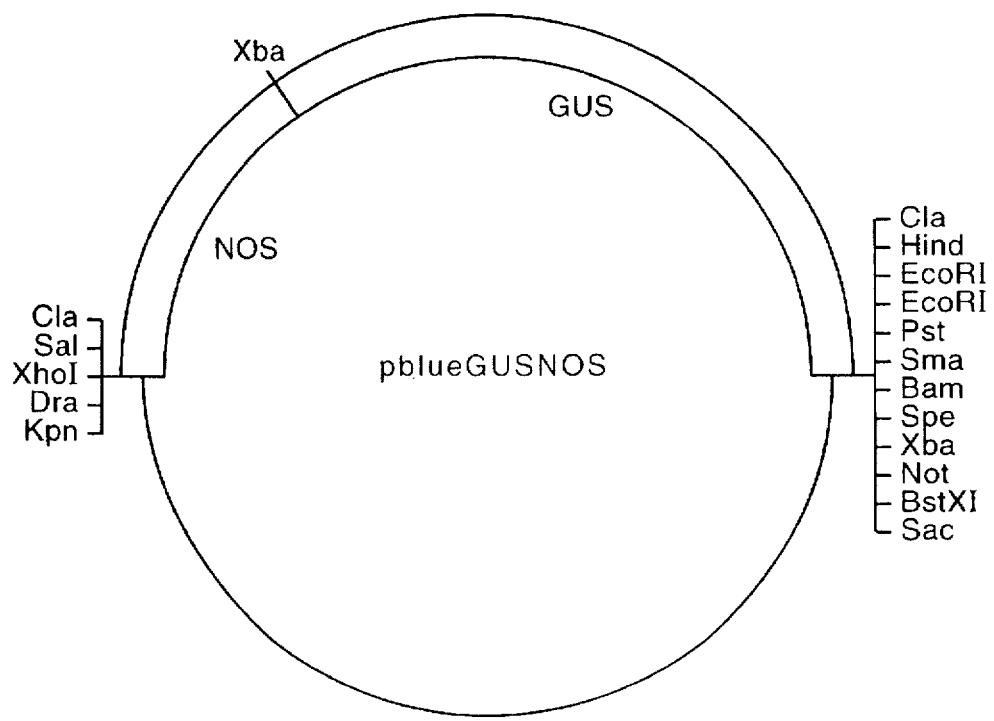
Figure 12:
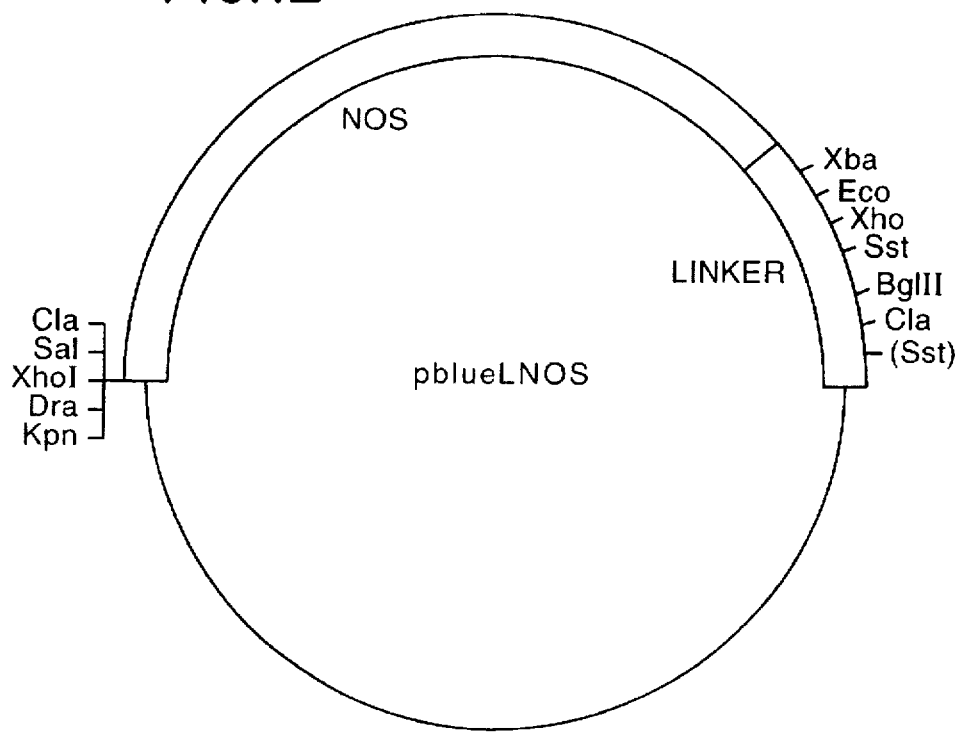
Figure 13:
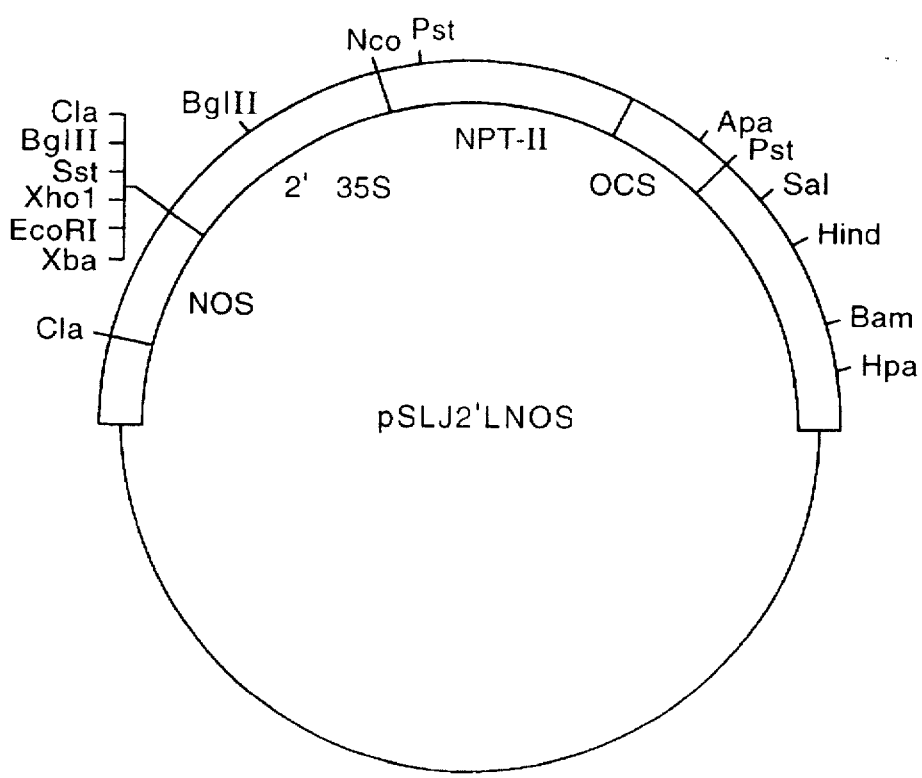

Expression of Nasturtium Xyloglucanase Sense and Antisense Sequences in Transgenic Plants a) Construction of pSLJ2'LNOS The vector pSLJ1006 (reference 13) was digested with the restriction enzyme Cla1 (FIG. 10). The 2008 bp DNA fragment (beta-glucuronidase [GUS] gene plus nopaline synthase [NOS] 3' termination sequence) was recovered and ligated into Cla1 linearised Bluescript SK+ to make pBLUE-GUS-NOS (FIG. 11). This vector was digested with the restriction enzymes Xba and Sst 1 and the 1852 bp GUS gene fragment replaced by the polylinker sequence (—Xba-EcoR1-Xho1-Sst1-Bgl2-Cla1—):

```
5'  CTAGAGAATTCTCGAGAGCTCAGATCTATCGATAGCT 3'
    (Seq. ID No. 14)
3'       TCTTAAGAGCTCTCGAGTCTAGATAGCTA      5'
    (Seq. ID No. 15)
``` generating pBLUE-L-NOS (FIG. 12). pSLJ2'LNOS (FIG. 13) was constructed by recovering the linker NOS (L-NOS) fragment from pBLUE-L-NOS using Cla1, and ligating this with the large (vector portion) Cla1fragment of pSLJ1006.

b) Construction of pSLJGXN-S

Figure 14:
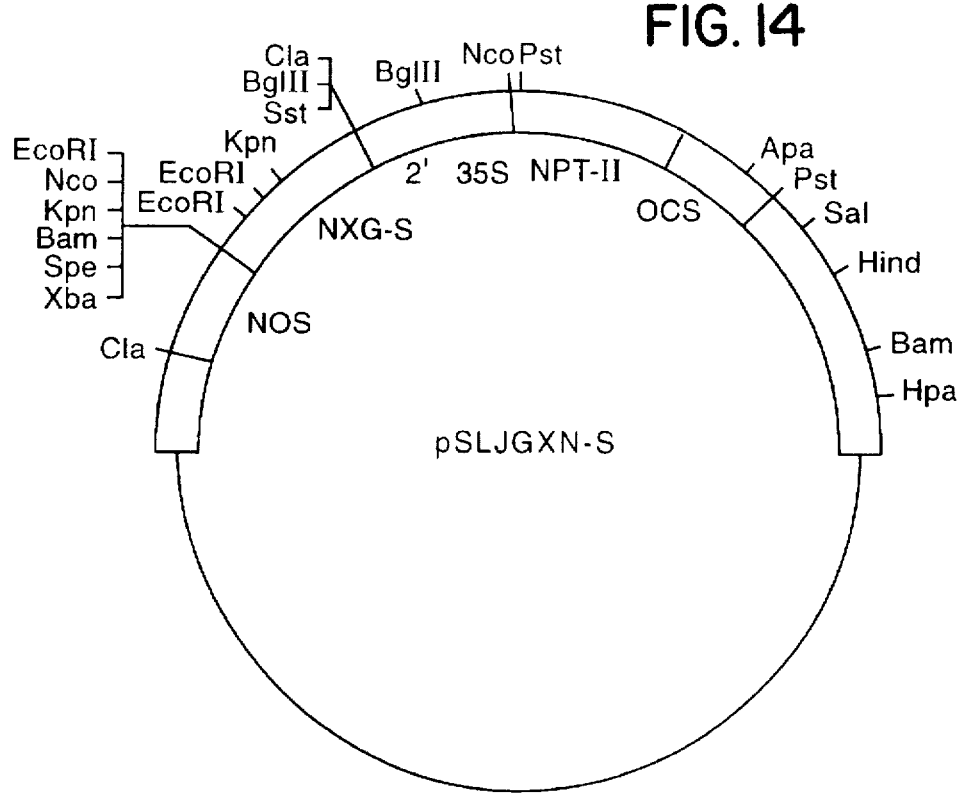
Figure 15:
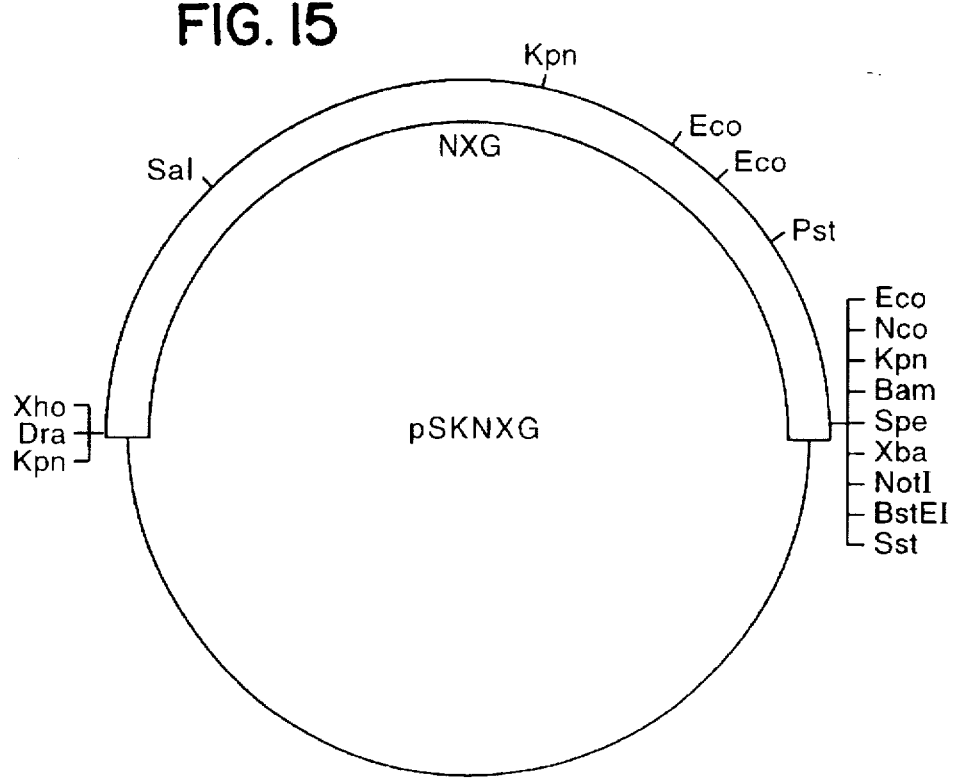

The vector pSLJGXN-S (FIG. 14) was prepared by inserting the nasturtium xyloglucanase coding region on an Xba-Sal1 DNA fragment from pSKNXG (FIG. 15, which plasmid was described previously with reference to FIG. 8), into the vector pSLJ2'LNOS, digested with the enzymes Xho1 and Xba.

c) Construction of pSLJGXN-X

Figure 16:
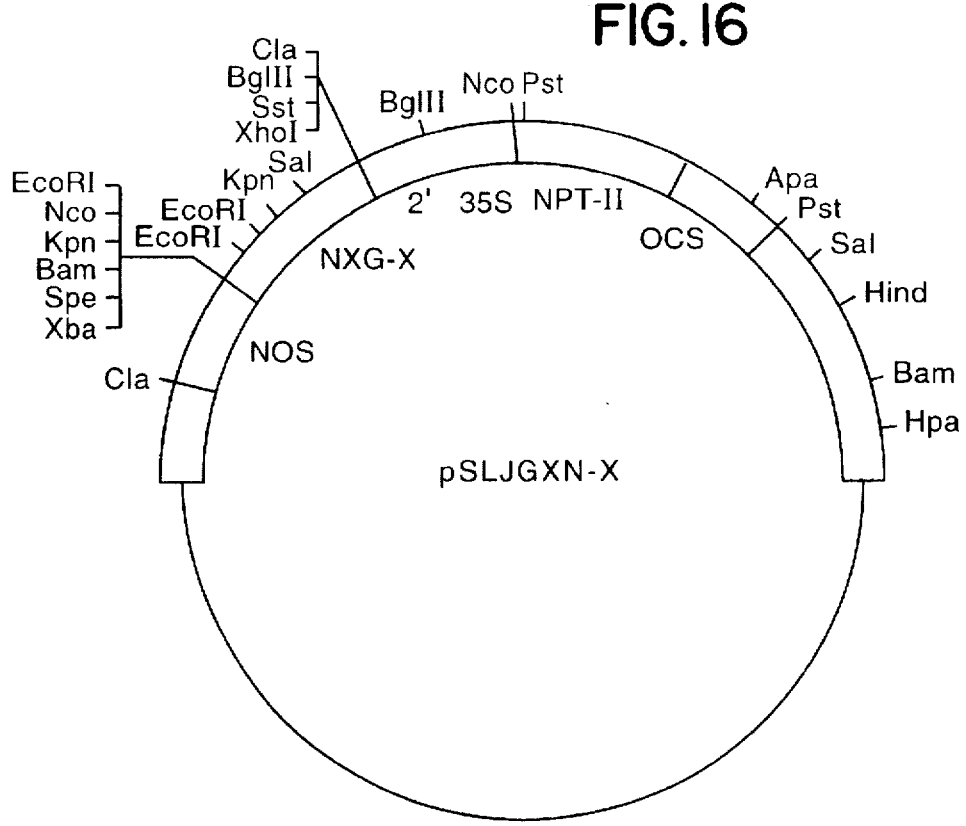

The vector pSLJGXN-X (FIG. 16) was made by inserting the nasturtium xyloglucanase coding region on an Xba - Sal1 DNA fragment from pSKNXG, into the corresponding sites of vector pSLJ2'LNOS.

d) Construction of pSLJNXG

Figure 17:
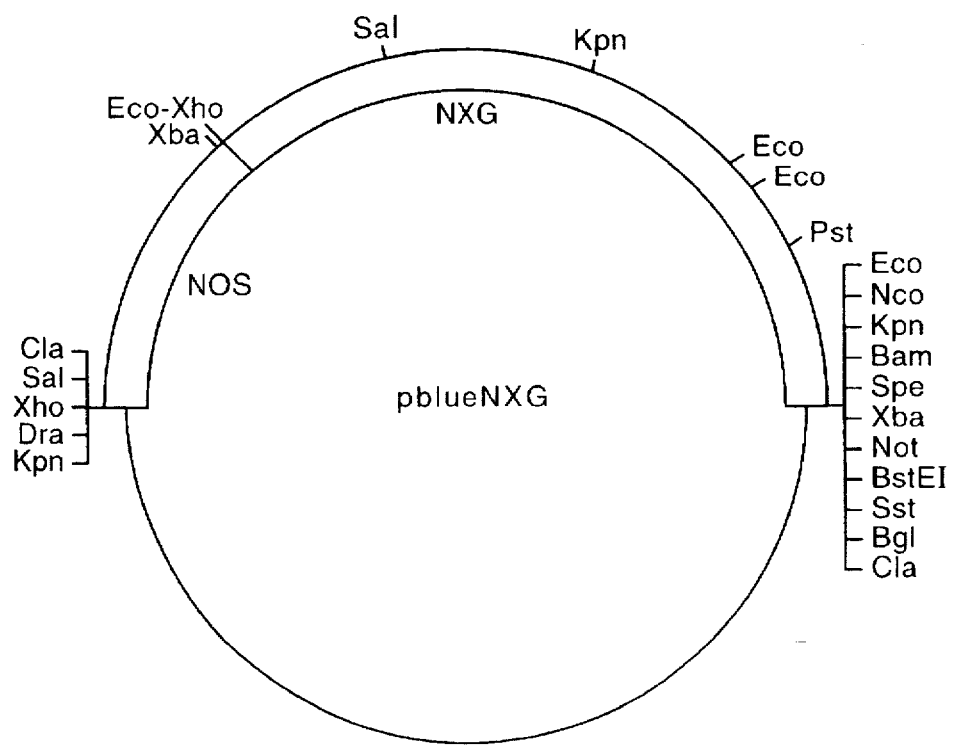
Figure 18:
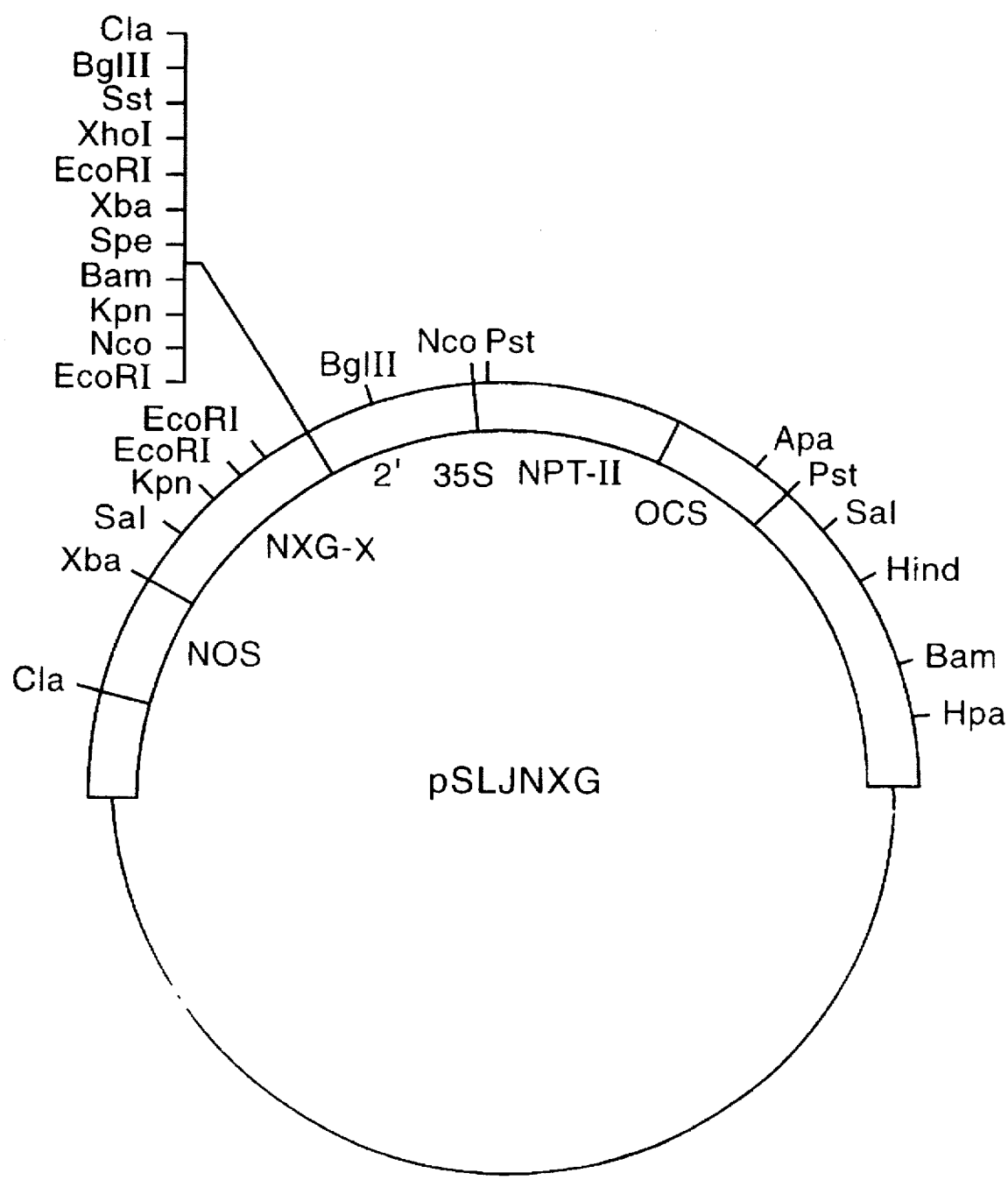

The vector pBLUE-NXG (FIG. 17) was constructed by digesting the plasmid pSKNXG with Xho1 (cohesive ends blunted) and Sst1 and transferring the NXG fragment into the vector portion of pBLUE-L-NOS, digested with EcoR1 (cohesive ends blunted) and Sst1. The xyloglucanase coding region was then transferred on an Xba DNA fragment from pBLUE-NXG to Xba linearised pSLJ2'LNOS. Resultant clones were screened for insertion of the xyloglucanase gene fragment in the sense orientation (pSLJNXG) (FIG. 18).

The T-DNA constructs described above were transferred into *Agrobacterium tumefaciens* strain LBA 4404 and then used to transform tobacco leaf discs or tomato cotyledonary segments using standard plant transformation procedures. Transfer of intact T-DNA fragments was confirmed using PCR/genomic Southern blot analysis (data not shown).

Expression of the sense sequence under the control of constitutive or suitable inducible (e.g. developmentally-regulated) promoter sequences will result in the production of xyloglucanase mRNA which will be translated to increase xyloglucanase enzyme levels in the transgenic plant.

Expression of the antisense gene under the control of constitutive or inducible promoter sequences will result in the production of mRNA which is complementary to endogenous xyloglucanase mRNA. The endogenous and antisense mRNAs, sharing a sufficient level of DNA homology with one another, will form an RNA complex, which may interfere with the normal transcription, processing, transport or translation of the endogenous mRNA. Alternatively the double stranded RNA complex, being unstable, will be degraded.

Antisense gene technology has been proven to work both at the gross visible phenotypic level e.g. lack of anthocyanin production in flower petals of petunia, leading to colourless flowers instead of coloured petals (reference 14) and at the biochemical level e.g. change in the amount of polygalacturonidase and reduction in depolymerisation of pectin during tomato fruit ripening (reference 8).

Using this approach target crop levels of xyloglucan endo-xyloglucanases can be altered. The nasturtium anti-xyloglucanase antibody can be used to determine levels of xyloglucanase in the transformed plant tissues. Altered levels of xyloglucanase can then be correlated with altered phenotypic characteristics, e.g.: growth rate, abscission or texture and storage properties (for either fruit or vegetables).

REFERENCES

1. R R Selvendran & J A Robertson. Cell Walls—components in the understanding of food texture and dietary fibres. IFR Report 1989.

2. P Albersheim. The walls of growing plant cells. Sci. Am. 232, 81–95, 1975.

3. P Albersheim. The primary cell wall. Plant Biochem 3rd Edition (Bonner and Varner), Ac. Press, 1976.

4. T Hyashi. Xyloglucans in the primary cell wall. Ann Rev Plant Physiol & Plant Mol Biol, 40, 139–168, 1989.

5. P R Crookes & D Grierson. Ultrastructure of tomato ripening and the role of polygalacturonase isoenzymes in cell wall degradation. Plant Physiol, 72, 1088–1093, 1983.

6. S Fry. Cross-linking of matrix polymers in the growing cell walls of Angiosperms. Ann Rev Plant Physiol, 37, 165–186, 1986.

7. C R Bird et al. The tomato polygalacturonase gene and ripening specific expression in transgenic plants. Plant Mol Biol, 11, 651–662, 1988.

8. Smith et al. Inhibition and effect on ripening of antisense polygalacturonase genes in transgenic tomatoes. Plant Mol Biol, 14, 369–379, 1990.

9. L G Cass et al. Isolation and characterisation of a cellulase gene family member expressed during avocado fruit ripening. Mol Gen Genet, 223, 76–86, 1990.

10. M L Tucker & S B Milligan. Sequence analysis and comparison of avocado fruit and bean abscission cellulases. Plant Physiol, 95, 928–933, 1991.

11. M Edwards et al. Purification and properties of a novel xyloglucan specific endo-(1–4)-Beta-D-glucanase from germinating nasturtium (*Tropaeolum majus* L.) seeds. J. Biol Chem, 261, 9494, 1986.

12. T C Hall et al. Messenger RNA for G1 protein of french bean seeds: cell free translation and product characterisation. P.N.A.S., 75, 3196–3200, 1978.

13. J Jones et al. Effective vectors for transformation, expression of heterologous genes, and assaying transposon excision in transgenic plants. Transgenic research, 1, 285–297, 1992.

14. van der Krol et al. Nature, 333, 866–869, 1988.

15. K Wakabayashi et al. Differential effect of auxin on molecular weight distributions of xyloglucans in cell walls of outer and inner tissues from segments of dark grown squash (Cucurbita maxima Duch.) hypocotyls. Plant Physiol, 95, 1070–1076, 1991.

16. T Hyashi. Xyloglucans in the primary cell wall. Ann Rev Plant Physiol & Plant Mol Biol, 40, 139–168, 1989.

17. D J Huber. Polyuronide degradation and hemicellulose modifications in ripening tomato fruit. J. Amer Soc Hort Sci, 108(3), 405–409, 1983.

18. C Fanutti et al. Action of a pure xyloglucan endotransglycosylase (formerly called xyloglucan-specific endo-(1–4)-beta-D-glucanase from the cotyledons of germinating nasturtium seeds. the Plant Journal (in press).

19. S C Fry et al. Xyloglucan endotransglycosylase, a new wall-loosening enzyme activity from plants. Biochem. J. 282, 821–829, 1992.

20. G Machlachlan and C Brady. Multiple forms of 1,4-beta-glucanase in ripening tomato fruits including a xyloglucanase activatable by xyloglucan oligosaccharides. Aust. J Plant Physiol, 19, 137–146, 1992.

SEQUENCE LISTING ( 1 ) GENERAL INFORMATION:

( i i i ) NUMBER OF SEQUENCES: 15

( 2 ) INFORMATION FOR SEQ ID NO: 1:

( i ) SEQUENCE CHARACTERISTICS:
        ( A ) LENGTH: 1229 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO ( i i i ) ANTI-SENSE: NO ( x i ) SEQUENCE DESCRIPTION: SEQ ID NO: 1:

```
CCTTATTCAC TTCACAAATG CCTTCTCCCT CCATAATGCC TCCTAACATT CTATCCATTT    60
TTCTTCATCT TCTTCCTATT CTAATGTTTT CTTCAAGCTG TTTGGGTCAG GGCCCACCTT   120
CACCAGGATA TTACCCTAGT AGCCAAATCA CTTCCCTAGG CTTTGATCAA GGCTATACAA   180
ATTTATGGGG TCCTCAACAT CAAAGGGTAG ACCAAGGCTC ATTAACAATA TGGCTTGATT   240
CTACCTCAGG AAGTGGATTC AAATCGATTA ACCGATATCG CTCTGGTTAC TTCGGTGCTA   300
ATATTAAGTT ACAATCTGGA TACACTGCAG GAGTCATTAC ATCTTTCTAT CTTTCGAATA   360
ACCAAGACTA TCCAGGAAAA CATGATGAGA TCGATATTGA ATTCCTCGGA ACAATACCCG   420
GAAAGCCGTA TACATTGCAG ACGAATGTTT TTATAGAAGG AAGTGGAGAT TACAATATAA   480
TCGGAAGGGA AATGAGAATT CATTTATGGT TTGATCCAAC ACAAGATTAT CATAACTATG   540
CTATTTATTG GACACCAAGT GAGATCATAT TTTTTGTCGA TGATGTACCG ATAAGGAGGT   600
ACCCTAGAAA GAGCGATGCT ACATTTCCTT TGAGACCGTT ATGGGTGTAC GGGTCGGTGT   660
GGGACGCGTC TTCTTGGGCT ACTGAAAACG GTAAATACAA AGCCGATTAT CGATACCAAC   720
CTTTTGTTGG AAAGTACGAA GATTTCAAGT TAGGTTCGTG CACCGTGGAA GCGGCTTCGT   780
CTTGCAATCC GGCTTCGGTA TCACCTTATG GTCAGTTGAG CCAACAACAA GTCGCGGCGA   840
TGGAATGGGT TCAGAAAAAT TACATGGTTT ATAATTATTG TGATGACCCG ACACGAGACC   900
ACACGTTAAC ACCCGAGTGT TAAGATTTCA TGTCGACTAA AAAACACAG CAAAAGAACA   960
AAAAGTTTTA TGGGTTTCAA TAATTTTTCT GAAAAAAAA TGATTTTTCT ATTTGGATTT  1020
AATTTGATAA AAAAAAAAAA AGGGTTTGTT GTTGTTGTTG TTTAATAATG GATGACTTGA  1080
```

| GATGGGTCTA | CTTGCCAAGA | AAAAGGTGCA | AGAGTTGTTG | GGCGTCCAAG | CATTCAAGAA | 1140 |
| CTTTGAAGGT | TATGTTGGGG | GCTGTTTTGT | TTTTTTTTA | ATATATGTAT | AATTGATCAT | 1200 |
| CTTTTATATT | TTAAATGAAT | TTATTGAAT | | | | 1229 |

( 2 ) INFORMATION FOR SEQ ID NO: 2:

( i ) SEQUENCE CHARACTERISTICS:
        ( A ) LENGTH: 938 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO ( x i ) SEQUENCE DESCRIPTION: SEQ ID NO: 2:

| CTTTCGAATA | ATCAAGACTA | TCCAGGAAAA | CATGATGAAA | TCGATATTGA | ATTTCTCGGA | 60 |
| ACAATACCTG | GAAAGCCGTA | TACATTGCAG | ACGAATGTTT | TCATAGAAGG | AAGTGGAGAT | 120 |
| TACAATATAA | TCGGAAGAGA | ATTGAGAATT | CATTTATGGT | TTGATCCAAC | ACAAGATTAT | 180 |
| CATAACTATG | CTATTTATTG | GACACCAAGT | GAGATCATAT | TTTTGTCGA | TGATGTACCG | 240 |
| ATAAGGAGGT | ACCCTAGAAA | GAGCGATGCT | ACATTTCCTT | TGAGACCGTT | ATGGGTGTAC | 300 |
| GGGTCGGTGT | GGGACGCGTC | TTCTTGGGCT | ACTGAAAACG | GTAAATACAA | AGCCGATTAT | 360 |
| CGATACCAAC | CTTTTGTTGG | AAAGTACGAA | GATTTCAAGT | TAGGTTCGTG | CACCGTGGAA | 420 |
| GCGGCTTCGT | CTTGCAATCC | GGCTTCGGTA | TCACCTTATG | GTCAGTTGAG | CCAACAACAA | 480 |
| GTCGCCGCGA | TGGAATGGGT | TCAGAAAAAT | TACATGGTTT | ATAATTATTG | TGATGACCCG | 540 |
| ACACGAGACC | ACACGTTAAC | ACCCGAGTGT | TAAGATTTCA | TGTCGACTAA | AAAACACTG | 600 |
| CAAAAGAACA | AAATGTTTTA | TGGGTTTCAA | TATTTTTTCT | GAAAAAAAAT | GATTTCTAT | 660 |
| TTGGATTTAA | TTTGATAAAA | AAAAGGGTTT | GTTGTTGTTG | TTGTTGTTTA | ATAATGGATG | 720 |
| ACTTGAGATG | GGTCTACTTG | CCAAGAAAAA | GGTGCAAGAG | TTGTTGGGCG | ATCGTCCAAG | 780 |
| CATTCAAGAA | CTTTGAAGGT | TATGTTGTGT | GCTGTTTTTT | TTTAATATA | TGTATAATTG | 840 |
| ATCATCTTTT | TTATTTAAA | TTAAGTTATT | GAATTATAT | ATATATATGT | ATATATATAT | 900 |
| ATGAATAAAA | GGTATATGTA | AGTTATATAT | AGAAGCTT | | | 938 |

( 2 ) INFORMATION FOR SEQ ID NO: 3:

( i ) SEQUENCE CHARACTERISTICS:
        ( A ) LENGTH: 295 amino acids
        ( B ) TYPE: amino acid
        ( C ) STRANDEDNESS: single
        ( D ) TOPOLOGY: unknown ( i i ) MOLECULE TYPE: protein ( i i i ) HYPOTHETICAL: NO ( x i ) SEQUENCE DESCRIPTION: SEQ ID NO: 3:

```
Met Pro Pro Asn Ile Leu Ser Ile Phe Leu His Leu Leu Pro Ile Leu
 1               5                   10                  15

Met Phe Ser Ser Ser Cys Leu Gly Gln Gly Pro Pro Ser Pro Gly Tyr
            20                  25                  30

Tyr Pro Ser Ser Gln Ile Thr Ser Leu Gly Phe Asp Gln Gly Tyr Thr
        35                  40                  45

Asn Leu Trp Gly Pro Gln His Gln Arg Val Asp Gln Gly Ser Leu Thr
    50                  55                  60
```

| Ile<br>65 | Trp | Leu | Asp | Ser | Thr<br>70 | Ser | Gly | Ser | Gly | Phe<br>75 | Lys | Ser | Ile | Asn | Arg<br>80 |
|---|---|---|---|---|---|---|---|---|---|---|---|---|---|---|---|
| Tyr | Arg | Ser | Gly | Tyr<br>85 | Phe | Gly | Ala | Asn | Ile<br>90 | Lys | Leu | Gln | Ser | Gly<br>95 | Tyr |
| Thr | Ala | Gly | Val<br>100 | Ile | Thr | Ser | Phe | Tyr<br>105 | Leu | Ser | Asn | Asn | Gln<br>110 | Asp | Tyr |
| Pro | Gly | Lys<br>115 | His | Asp | Glu | Ile<br>120 | Asp | Ile | Glu | Phe | Leu<br>125 | Gly | Thr | Ile | Pro |
| Gly | Lys<br>130 | Pro | Tyr | Thr | Leu | Gln<br>135 | Thr | Asn | Val | Phe | Ile<br>140 | Glu | Gly | Ser | Gly |
| Asp<br>145 | Tyr | Asn | Ile | Ile | Gly<br>150 | Arg | Glu | Met | Arg | Ile<br>155 | His | Leu | Trp | Phe | Asp<br>160 |
| Pro | Thr | Gln | Asp | Tyr<br>165 | His | Asn | Tyr | Ala | Ile<br>170 | Tyr | Trp | Thr | Pro | Ser<br>175 | Glu |
| Ile | Ile | Phe | Phe<br>180 | Val | Asp | Asp | Val | Pro<br>185 | Ile | Arg | Arg | Tyr | Pro<br>190 | Arg | Lys |
| Ser | Asp | Ala<br>195 | Thr | Phe | Pro | Leu | Arg<br>200 | Pro | Leu | Trp | Val | Tyr<br>205 | Gly | Ser | Val |
| Trp | Asp<br>210 | Ala | Ser | Ser | Trp | Ala<br>215 | Thr | Glu | Asn | Gly | Lys<br>220 | Tyr | Lys | Ala | Asp |
| Tyr<br>225 | Arg | Tyr | Gln | Pro | Phe<br>230 | Val | Gly | Lys | Tyr | Glu<br>235 | Asp | Phe | Lys | Leu | Gly<br>240 |
| Ser | Cys | Thr | Val | Glu<br>245 | Ala | Ala | Ser | Ser | Cys<br>250 | Asn | Pro | Ala | Ser | Val<br>255 | Ser |
| Pro | Tyr | Gly | Gln<br>260 | Leu | Ser | Gln | Gln | Gln<br>265 | Val | Ala | Ala | Met | Glu<br>270 | Trp | Val |
| Gln | Lys | Asn<br>275 | Tyr | Met | Val | Tyr | Asn<br>280 | Tyr | Cys | Asp | Asp | Pro<br>285 | Thr | Arg | Asp |
| His | Thr<br>290 | Leu | Thr | Pro | Glu | Cys<br>295 | | | | | | | | | |

( 2 ) INFORMATION FOR SEQ ID NO: 4:

( i ) SEQUENCE CHARACTERISTICS:
        ( A ) LENGTH: 20 amino acids
        ( B ) TYPE: amino acid
        ( C ) STRANDEDNESS: single
        ( D ) TOPOLOGY: unknown ( i i ) MOLECULE TYPE: peptide ( i i i ) HYPOTHETICAL: NO ( i i i ) ANTI-SENSE: NO ( v ) FRAGMENT TYPE: internal ( x i ) SEQUENCE DESCRIPTION: SEQ ID NO: 4:

| Asn<br>1 | Tyr | Met | Val | Tyr<br>5 | Asn | Tyr | Cys | Asp | Asp<br>10 | Pro | Thr | Arg | Asp | His<br>15 | Thr |
|---|---|---|---|---|---|---|---|---|---|---|---|---|---|---|---|
| Leu | Thr | Pro | Glu<br>20 | | | | | | | | | | | | |

( 2 ) INFORMATION FOR SEQ ID NO: 5:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear (  i  i  ) MOLECULE TYPE: DNA (genomic)

(  i  i  i  ) HYPOTHETICAL: NO (  i  i  i  ) ANTI-SENSE: YES (  x  i  ) SEQUENCE DESCRIPTION: SEQ ID NO: 5:

TTAATATACC ANATATTAAT                    20

( 2 ) INFORMATION FOR SEQ ID NO: 6:

(  i  ) SEQUENCE CHARACTERISTICS:
        ( A ) LENGTH: 15 amino acids
        ( B ) TYPE: amino acid
        ( C ) STRANDEDNESS: single
        ( D ) TOPOLOGY: unknown (  i  i  ) MOLECULE TYPE: peptide (  i  i  i  ) HYPOTHETICAL: NO (  v  ) FRAGMENT TYPE: internal (  x  i  ) SEQUENCE DESCRIPTION: SEQ ID NO: 6:

Ala  Asp  Tyr  Arg  Tyr  Gln  Pro  Phe  Val  Gly  Lys  Tyr  Glu  Asp  Phe
1                   5                             10                            15

( 2 ) INFORMATION FOR SEQ ID NO: 7:

(  i  ) SEQUENCE CHARACTERISTICS:
        ( A ) LENGTH: 19 amino acids
        ( B ) TYPE: amino acid
        ( C ) STRANDEDNESS: single
        ( D ) TOPOLOGY: unknown (  i  i  ) MOLECULE TYPE: peptide (  i  i  i  ) HYPOTHETICAL: NO (  v  ) FRAGMENT TYPE: internal (  x  i  ) SEQUENCE DESCRIPTION: SEQ ID NO: 7:

Leu  Gly  Ser  Cys  Thr  Val  Glu  Ala  Ala  Ser  Ser  Cys  Asn  Pro  Ala  Ser
1                   5                             10                            15

Val  Ser  Pro ( 2 ) INFORMATION FOR SEQ ID NO: 8:

(  i  ) SEQUENCE CHARACTERISTICS:
        ( A ) LENGTH: 10 amino acids
        ( B ) TYPE: amino acid
        ( C ) STRANDEDNESS: single
        ( D ) TOPOLOGY: unknown (  i  i  ) MOLECULE TYPE: peptide (  i  i  i  ) HYPOTHETICAL: NO (  v  ) FRAGMENT TYPE: internal (  x  i  ) SEQUENCE DESCRIPTION: SEQ ID NO: 8:

Ser  Asp  Ala  Thr  Phe  Pro  Leu  Arg  Pro  Leu
1                   5                             10

( 2 ) INFORMATION FOR SEQ ID NO: 9:

(  i  ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear (i i) MOLECULE TYPE: cDNA to mRNA (i i i) HYPOTHETICAL: NO (i i i) ANTI-SENSE: YES (x i) SEQUENCE DESCRIPTION: SEQ ID NO: 9:

CCAGGTATTG TTCCGAGAAA TTCAATATCG 30

(2) INFORMATION FOR SEQ ID NO: 10:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (i i) MOLECULE TYPE: cDNA to mRNA (i i i) HYPOTHETICAL: NO (i i i) ANTI-SENSE: YES (x i) SEQUENCE DESCRIPTION: SEQ ID NO: 10:

CCTGGATAGT CTTGATTATT CGA 23

(2) INFORMATION FOR SEQ ID NO: 11:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (i i) MOLECULE TYPE: cDNA to mRNA (i i i) HYPOTHETICAL: NO (i i i) ANTI-SENSE: NO (x i) SEQUENCE DESCRIPTION: SEQ ID NO: 11:

GACCATGATT ACGCCAAGCT C 21

(2) INFORMATION FOR SEQ ID NO: 12:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (i i) MOLECULE TYPE: cDNA to mRNA (i i i) HYPOTHETICAL: NO (i i i) ANTI-SENSE: YES (x i) SEQUENCE DESCRIPTION: SEQ ID NO: 12:

TGTTGTTGGC TCAACTGACC A 21

(2) INFORMATION FOR SEQ ID NO: 13:

(i) SEQUENCE CHARACTERISTICS:
        (A) LENGTH: 29 base pairs
        (B) TYPE: nucleic acid
        (C) STRANDEDNESS: single
        (D) TOPOLOGY: linear (i i) MOLECULE TYPE: cDNA to mRNA (i i i) HYPOTHETICAL: NO (i i i) ANTI-SENSE: NO (x i) SEQUENCE DESCRIPTION: SEQ ID NO: 13:

GAGGATCCTG GATAGTCTTG ATTATTCGA 29

(2) INFORMATION FOR SEQ ID NO: 14:

(i) SEQUENCE CHARACTERISTICS:
        (A) LENGTH: 37 base pairs
        (B) TYPE: nucleic acid
        (C) STRANDEDNESS: single
        (D) TOPOLOGY: linear (i i) MOLECULE TYPE: cDNA to mRNA (i i i) HYPOTHETICAL: NO (x i) SEQUENCE DESCRIPTION: SEQ ID NO: 14:

CTAGAGAATT CTCGAGAGCT CAGATCTATC GATAGCT 37

(2) INFORMATION FOR SEQ ID NO: 15:

(i) SEQUENCE CHARACTERISTICS:
        (A) LENGTH: 29 base pairs
        (B) TYPE: nucleic acid
        (C) STRANDEDNESS: single
        (D) TOPOLOGY: linear (i i) MOLECULE TYPE: cDNA to mRNA (i i i) HYPOTHETICAL: NO (x i) SEQUENCE DESCRIPTION: SEQ ID NO: 15:

ATCGATAGAT CTGAGCTCTC GAGAATTCT 29

We claim:

1. A nucleotide sequence encoding an enzyme having a xylogucan-specific endo-(1-4)-beta-D-glucanase activity, comprising nucleotides 35–919 of the sequence shown in FIGS. 9A and 9B (Seq. ID No. 1) or functional equivalents thereof encoding a polypeptide retaining said beta-D-glucanase activity.

2. A sequence according to claim 1, further comprising a 5' untranslated region.

3. A sequence according to claim 1 or 2, further comprising a 3' untranslated region.

4. A sequence according to claim 1, comprising the sequence obtainable from *Topaeolum majus* L.

5. A vector, comprising the sequence of claim 1.

6. A plant or part thereof, into which has been introduced the sequence of claim 1.

7. A method of altering the characteristics of a plant or a part thereof, comprising introducing the sequence of claim 1 into said plant or part thereof.

8. A method according to claim 7, wherein the said altered characteristic is selected from the group consisting of size, texture and speed of ripening.

9. A method according to claim 8, wherein the characteristics of a fruit or vegetable are altered.

10. A method according to claim 7, wherein the characteristics of a tomato plant or part thereof are altered.

11. A method of producing an enzyme having a xyloglucan-specific endo-(1-4)-beta-D-glucanase activity, comprising:

inserting the sequence of claim 1 into a suitable vector;

transforming an appropriate host cell with said vector;

growing said transformed host cell in suitable culture conditions such that the enzyme is expressed; and obtaining the enzyme from the culture medium and/or the host cells.

12. A method according to claim 11, wherein the host cell is a micro-organism.

13. A method according to claim 11 or 12, wherein the host cell is eukaryotic.

14. A vector according to claim 5, in which the sequence is operably linked in the antisense orientation to a promoter.

* * * * *